United States Patent [19]
Taheri

[11] Patent Number: 6,030,414
[45] Date of Patent: Feb. 29, 2000

[54] VARIABLE STENT AND METHOD FOR TREATMENT OF ARTERIAL DISEASE

[76] Inventor: Syde A. Taheri, 268 Dan-Troy, Williamsville, N.Y. 14221

[21] Appl. No.: 08/970,055

[22] Filed: Nov. 13, 1997

[51] Int. Cl.[7] .................................................. A61F 2/06
[52] U.S. Cl. .................................. 623/1; 623/11; 623/12
[58] Field of Search .................................. 623/1, 11, 12; 606/191–200, 153

[56] References Cited

U.S. PATENT DOCUMENTS

| | | | |
|---|---|---|---|
| 4,994,071 | 2/1991 | MacGregor | 606/194 |
| 5,653,743 | 8/1997 | Martin | 623/1 |
| 5,755,772 | 5/1998 | Evans et al. | 606/191 |
| 5,755,778 | 5/1998 | Kleshinski | 623/1 |

*Primary Examiner*—Mickey Yu
*Assistant Examiner*—Choon P. Koh
*Attorney, Agent, or Firm*—Hodgson Russ Andrews Wood & Goodyear LLP

[57] ABSTRACT

The present invention contemplates the use of a grafted stent having predetermined and sized lateral openings for the treatment of arterial disease at or around the intersection of multiple arteries, thereby ensuring blood flow through such arteries to collateral organs. In particular, the point of intersection of the arteries to be treated is determined and the lateral openings are interposed within the stent and appended graft and the stented graft is positioned precisely at a premeasured point whereby the intersection of the arteries coincides with the lateral openings of the stented graft. The method and apparatus of the present invention further includes securing the lateral openings of the stented graft against a portion of the walls of the intersection point to guard against leaking or improper fit.

4 Claims, 7 Drawing Sheets

FIG. 1
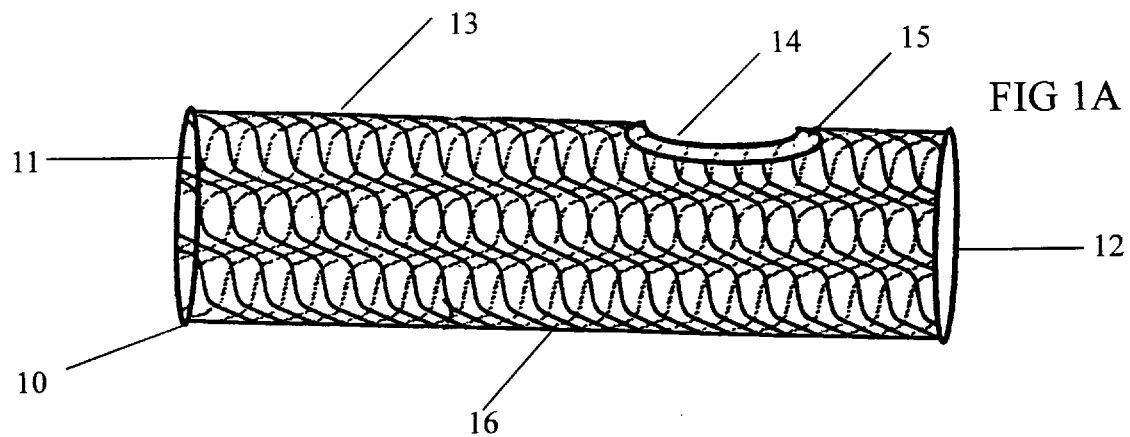
FIG 1A
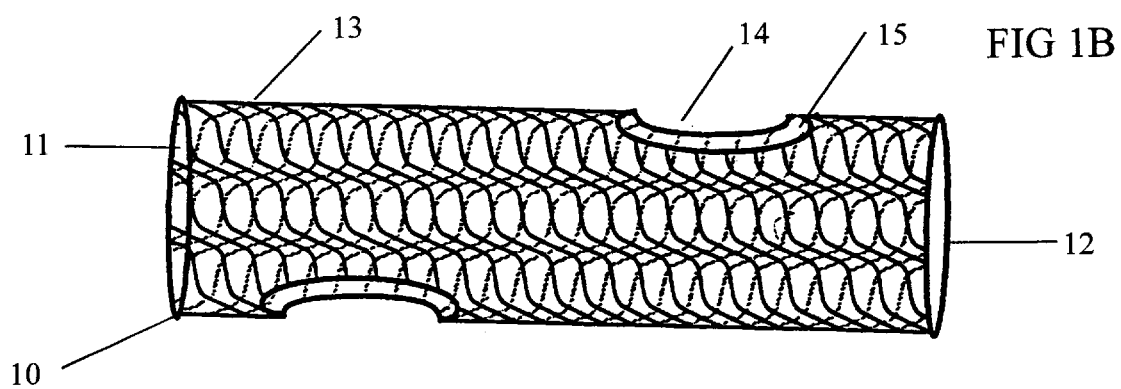
FIG 1B
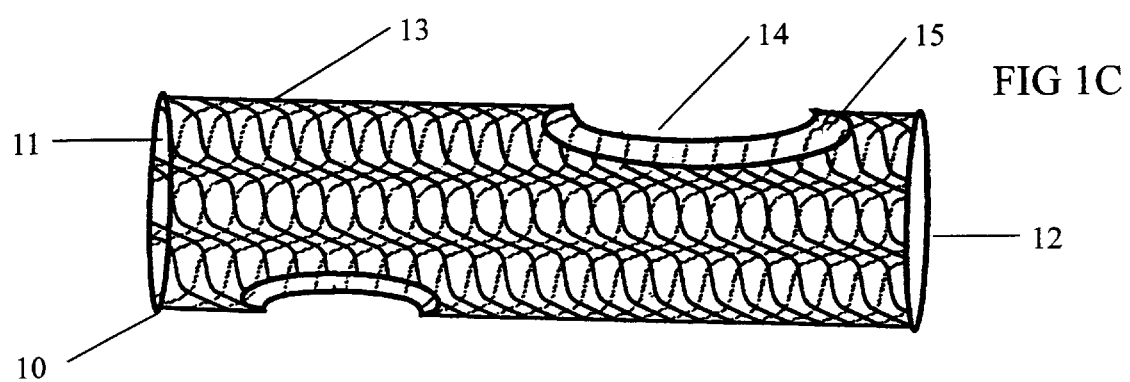
FIG 1C

VARIABLE STENT AND METHOD FOR TREATMENT OF ARTERIAL DISEASE

BACKGROUND OF THE INVENTION

The present invention relates generally to the treatment of arterial disease, including for example, aortic occlusive disease, and in particular, to an improved stent and method for treating arterial disease at or around the intersection of a plurality of arteries or blood flow passageways such as the intersection of the aorta and renal arteries or the aorta and posterior spinal arteries.

The prior art describes the treatment of arterial disease by various surgical techniques, some involving the use of stents and grafts. For example, it is well known in the art to interpose within the diseased portion of an artery a stent, whether made of stainless steel, nitinol or other materials, capable of being balloon-expandable for strengthening the walls of a stenotic or occluded artery. Similarly, it is also well known in the prior art to use a graft in conjunction with a stent to repair highly damaged portions of the aorta or other arteries thereby ensuring blood flow and reducing the risk of an aneurysm or rupture. Grafts, comprised of hollow tubes of material such as dacron, are normally inserted within the walls of a damaged artery and can be sewn into position or expanded through the use of a stented balloon catheter.

A more severe problem occurs when it is desirable to use a graft or a stent at or around the intersection of a major artery (e.g., the aorta) with intersecting arteries (e.g., the renal arteries). While the graft and stent is clearly preferred to strengthen and ensure the flow of blood through the aorta, the use of a stented graft effectively seals or blocks off the blood flow to collateral organs such as the kidneys. Accordingly, as described in U.S. Pat. No. 5,617,878 (Stent and Method for Treatment of Aortic Occlusive Disease), surgeons have devised various other techniques to repair weakened arterial walls in such cases including the use of a "bifurcated" stent comprised of a single stent and graft adapted through cutting to incorporate a second stent and graft. The technique, while effective, has proven cumbersome and somewhat difficult to employ and execute.

The present invention solves the problem of the prior art by providing a novel and improved device and method for treating arterial disease through the use of stented grafts at or around the intersection point of an occluded or diseased artery and another artery.

SUMMARY OF THE INVENTION

The present invention comprises a novel method and improved stent and graft for use in the surgical treatment of arterial disease and in particular, a novel method and improved stent and graft for treating arterial disease at or around the intersection of various major arteries; e.g., the aorta and renal arteries or brachycephalic arteries. The improved stent and graft combination comprises a typical and well-known strengthened mesh body portion, adapted to be contracted and expanded through either stress or temperature. The stent of the present invention is of cylindrical shape and has a series of "zig-zag" or "stepped" sections required for effective contraction and expansion for delivery into a particular artery through the use of a well-known balloon catheter. The stent is adapted to be received within a graft well-known in the art. The stent and graft of the present invention also comprises a plurality of lateral openings along the surface of the stent and accompanying graft. These openings are strengthened through the use of a collar portion on the body of the stent. The openings are positioned at a point along the length of the stent and graft corresponding to a pre-measured point of intersection between the arteries to be treated. The stent and graft combination have superimposed coincident lateral openings at various points along their length.

The stent and graft combination is delivered using a balloon catheter and is placed in position such that the opening of an intersecting artery corresponds to the lateral openings of the stent and graft combination thereby permitting longitudinal blood flow through the stent graft combination and, as well, through the lateral opening into the intersecting artery.

The method of the present invention includes first measuring through the use of well-known techniques such as ultrasound or other imaging the exact location of the intersection of the two arteries to be treated. The size or diameter of the intersection point is also measured and the lateral openings of the graft and stent combination are sized and positioned accordingly to accommodate the artery at the point of intersection. A stent and graft combination of appropriate size is provided and is inserted into the primary artery to be treated such that the lateral openings of the stent and graft combination correspond to the point of arterial intersection. A balloon catheter is then used to expand the stent and graft combination against the walls of the primary artery to be treated and, as well, to press the support ring of the stent against the lateral opening of the graft and against the arterial wall at or around the point of intersection to ensure the integrity of the point of intersection to be treated. When properly positioned, the stent and graft combination is firmly affixed against the walls of the artery to be treated and, as well, forms a tight seal at the point of intersection of the two arteries through the use of the lateral openings and support collar. Blood is able to flow through both passageways thereby permitting the use of the stent and graft technique at or around the intersection of a diseased artery.

Accordingly, one object of the present invention is to provide a stent and a unique method for repairing and strengthening a diseased artery at or around a point of arterial intersection.

Another object of the invention is to provide an improved stent having lateral openings and adapted to be used with a corresponding graft for the treatment of arterial disease at or around the intersection of two or more arteries.

Yet another object of the invention is to provide a method and corresponding apparatus for the treatment of arterial disease at or around the intersection of two or more arteries that simplifies the required surgical technique and treatment procedure.

These and other objects of the invention will be apparent to one of ordinary skill in the art from the specification, the drawing figures and the claims that follow.

DESCRIPTION OF THE DRAWING FIGURES

FIG. 1, comprising FIGS. 1A, 1B and 1C are views of the stent of the present invention generally showing the lateral openings.

DESCRIPTION OF THE PREFERRED EMBODIMENT OF THE INVENTION

Figure 2:
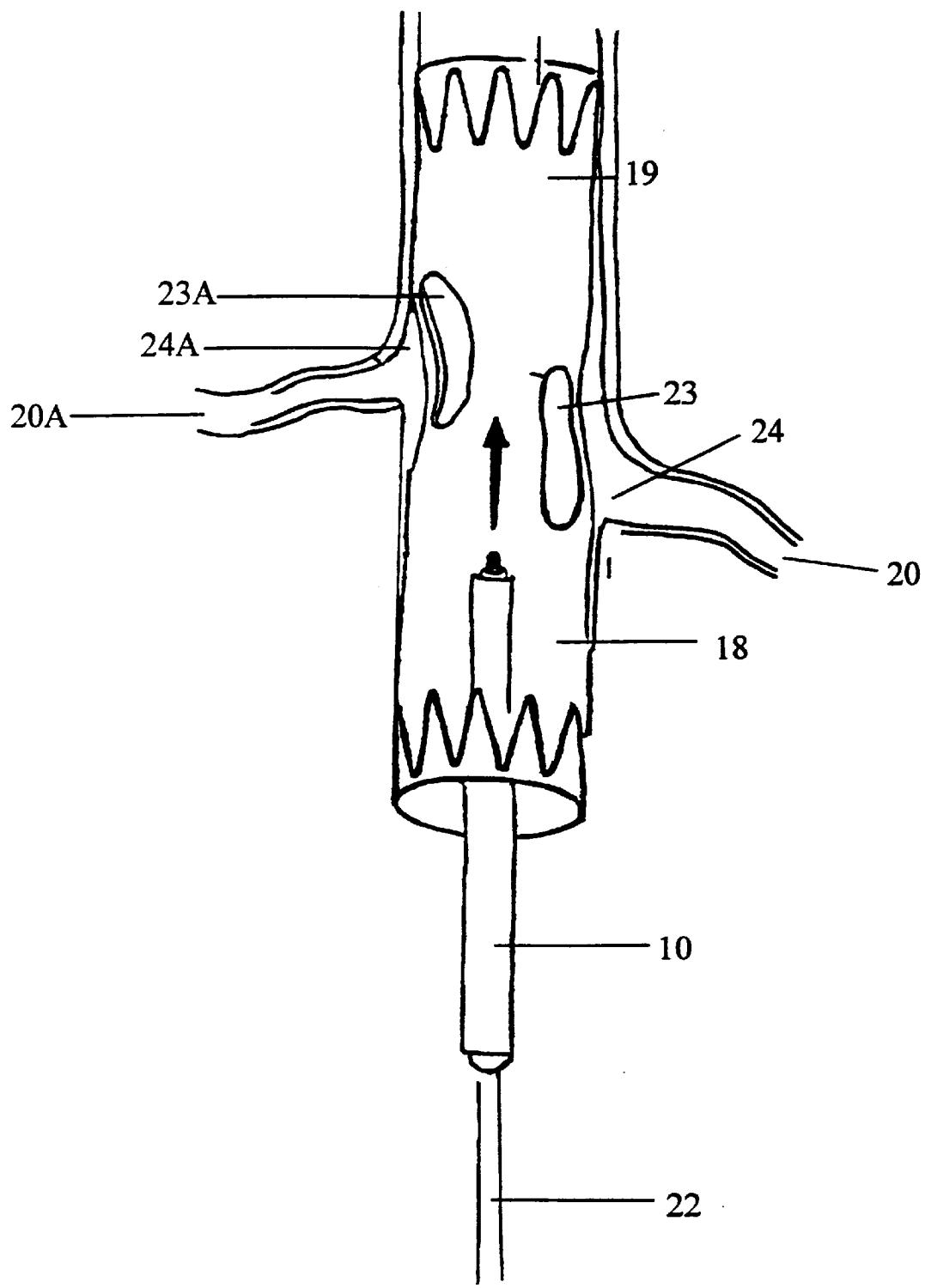
FIG. 2 is a view of the intersection of three arteries and the insertion of a graft and stent combination through the use of a balloon catheter.

The present invention describes a novel method and stented graft for use in the treatment of arterial disease at or around the intersection of multiple arteries, such as the renal arteries to the kidneys or brachycephalic artery and carotid artery to the brain. The present invention simply and efficiently solves the problems in the prior art with the use of graft/stent combinations at or around the intersection of diseased arteries and provides a straightforward and simple method for treatment in such cases.

In particular, the method and attendant device of the present invention relies upon a surgeon's present ability to visualize and precisely measure the location of the intersection of diseased arteries through the use of well-known visualization techniques common in the art. In general, once the precise location of the intersection point and the size of the diseased arterial intersection are known, the present invention contemplates use of a graft or graft/stent combination having lateral openings adapted to be positioned at the point of intersection such that blood is capable of flowing longitudinally through the grafted stent and, as well, into collateral or intersecting arteries without impediment. The invention further includes the capability of firmly securing predefined lateral openings in the stent/graft combination to the walls of the diseased artery at the point of intersection to avoid leaking or reduced blood flow.

Both the novel method and apparatus of the present invention are illustrated in the accompanying drawing figures.

Adverting first to FIGS. 1A, 1B and 1C, the stent of the present invention is illustrated and described. In particular, stent 10 is shown to include substantially circular and opposed openings, 11 and 12, joined by a cylindrical body portion, 13. Stent 10 also includes along its body portion a plurality of substantially circular lateral openings, 14, supported and further defined by a lateral support ring, 15. Lateral support ring 15, which can be constructed of a variety of materials (e.g., plastic, steel), serves to support and define lateral opening 14 upon insertion of the stent into an artery to be treated.

Continuing to advert to FIGS. 1A through C, body portion 13 of stent 10 is shown to be formed of a series of connecting wire "steps" adapted to render the stent flexible and, as well, capable of being reduced in dimension for insertion into various delivery devices such as a catheter or lumen and attendant balloon. These delivery systems are well-known in the art. Moreover, it is also well-known in the art to construct stents of various materials such as stainless steel or nitinol, capable of being reduced in size by stress or temperature and, upon delivery to a diseased artery, capable of being reformed to their original size and shape.

The lateral openings, 14, of stent, 10, are positioned along stent body portion, 13, at points corresponding to the measured position of the intersection of a diseased artery with the artery to be treated. Moreover, the diameter of stent lateral opening, 14, together with support ring, 15, is constructed to be slightly larger than the opening of the intersecting artery communicating with the diseased artery to be treated.

Further, stent 10 is adapted to fit within a graft (see reference 18 of FIG. 2) as is well-known in the art. The combination of graft 18 and stent 10 can be accomplished prior to insertion through the use of common and well-known insertion means or, alternatively, stent 10 can be interposed within graft 18 after the graft is already in place within the artery to be treated.

Adverting next to FIG. 2, graft 18 is shown to be inserted into artery 19 (e.g., the ascending aorta) at a point of intersection of two lateral arteries, 20 and 20A. Intersecting arteries 20 and 20A are shown to have openings 24 and 24A respectively each having a specific diameter capable of being measured with precision prior to insertion of graft 18.

Graft 18 also includes prepositioned lateral openings 23 and 23A placed along the graft at a premeasured location corresponding to the location of the intersection of lateral arteries 20 and 20A with diseased artery 19. Delivery system 22 (e.g., a balloon catheter) is further shown with engaged stent, 10, as it is about to be inserted into graft 18, already in place.

Figure 3:
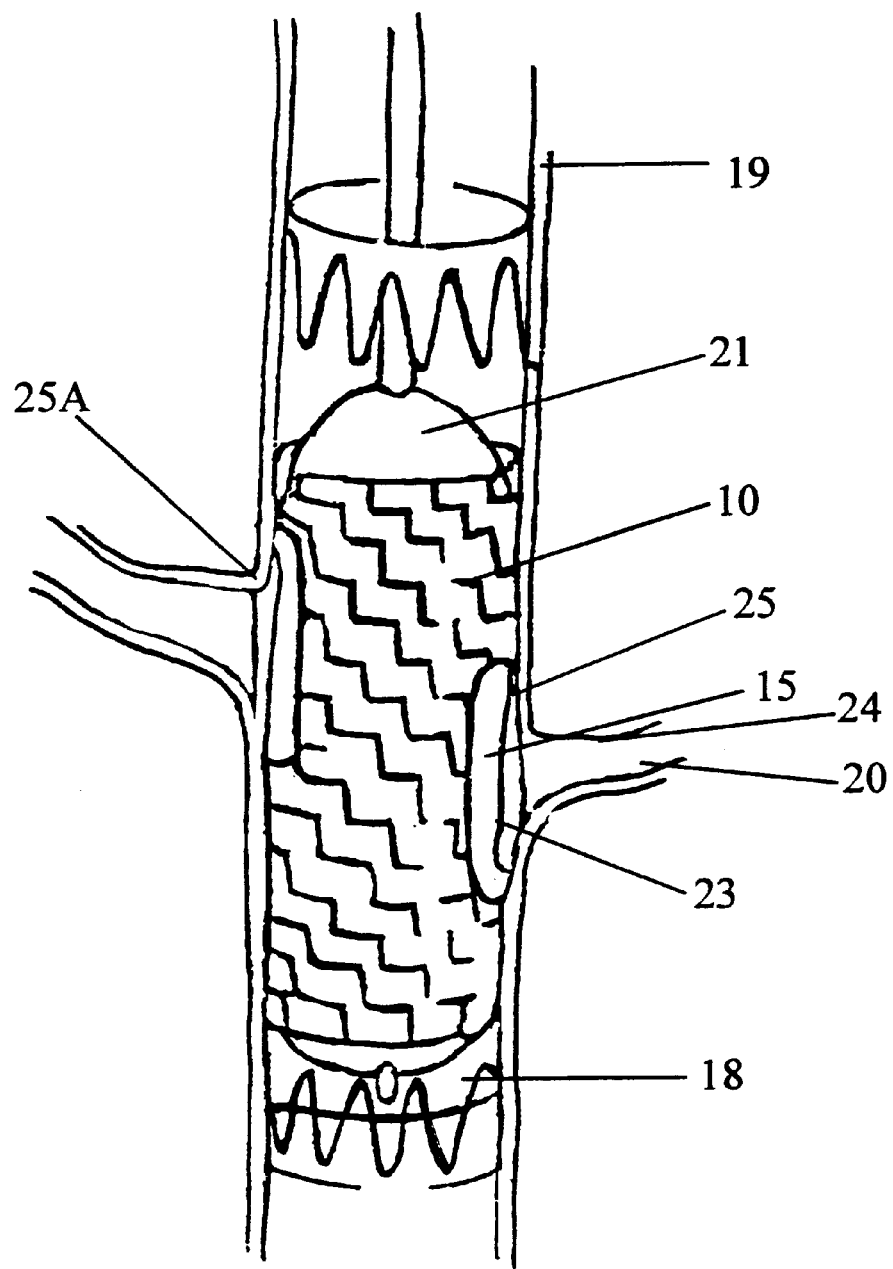
FIG. 3 is a view of the intersection of three arteries having the stent and graft of the present invention interposed therein and expanded through the use of a balloon catheter.

Adverting next to FIG. 3, stent 10 is shown to be expanded within graft 18 at or around the diseased area of artery 19. Expansion and positioning of stent 10 is accomplished through the use of balloon catheter 21 which expands stent 10 against the inner wall of graft 18. The expansion of stent 10 within graft 18 is only undertaken after the stent is positioned such that the lateral openings of the stent and graft are coincident, thereby ensuring a lateral passageway for blood flow. When stent 10 is expanded, ring 15 is not only pressed against the inside opening of graft 18 but also is measured such that it tightly intersects wall portions 25 and 25A of artery 19 at or around the intersection point, 24, of artery 20 and artery 19. This ensures the coincident lateral openings of the stent and graft are firmly affixed to the inside wall of artery 19 at the appropriate point such that blood flow not only freely proceeds through the longitudinal axis of the stent and graft, but also, laterally to the intersecting arteries.

Figure 4:
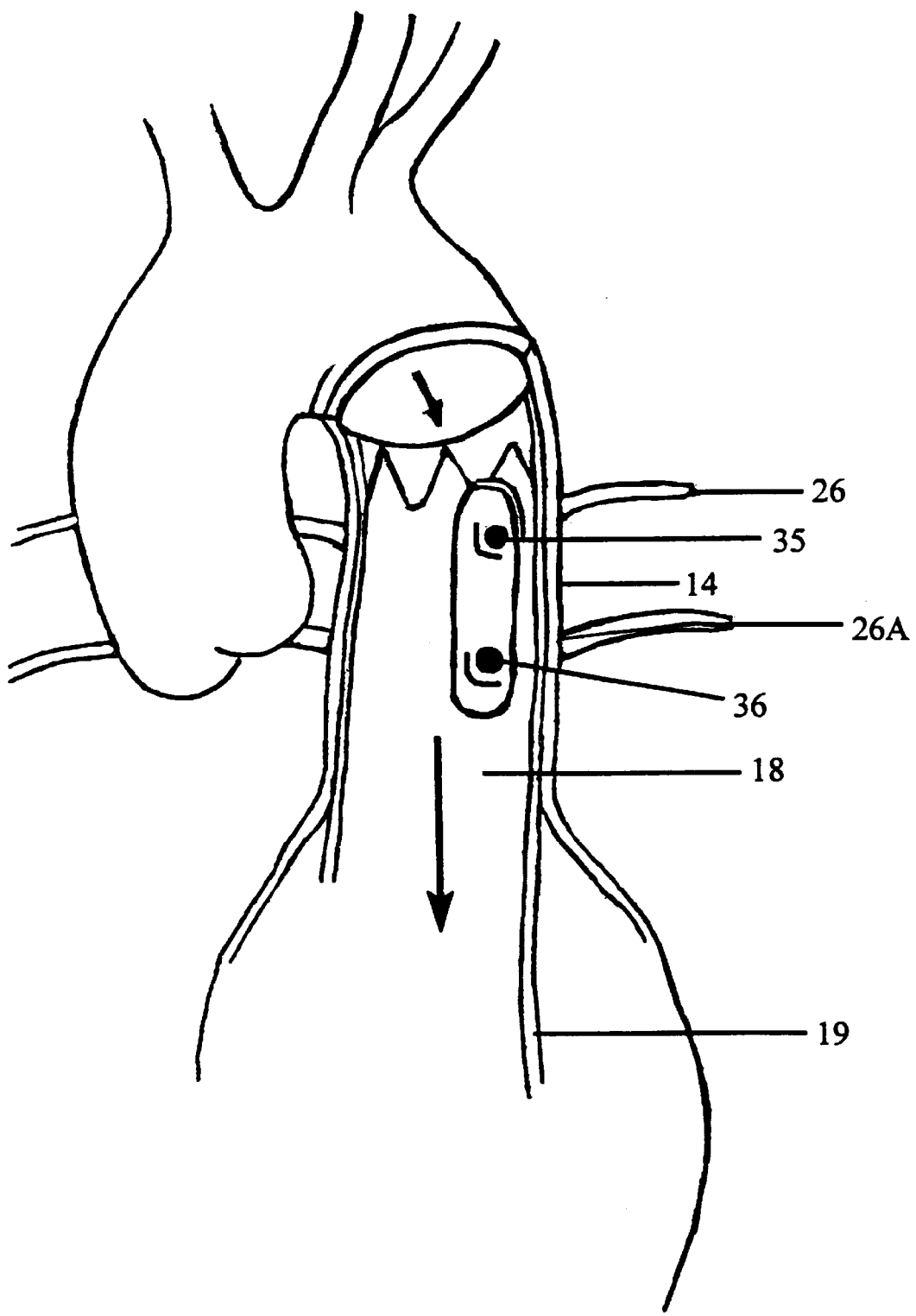
FIG. 4 is a partial sectional view of the stent and graft of the present invention interposed at the intersection of the descending aorta and posterior spinal arteries.

FIGS. 4, 5, 6, 7, and 8 further describe use of the device and novel method of the present invention in the context of the treatment of arterial disease at common arterial intersection points. For example, FIG. 4 illustrates the use of the present stented graft combination 18 interposed within descending aorta 19 at or around the intersection point of posterior spinal arteries, 26 and 26A. By way of partial sectional view, the stented graft combination is shown to accommodate the intersection of points, 35 and 36, of posterior spinal arteries 26 and 26A.

Figure 5:
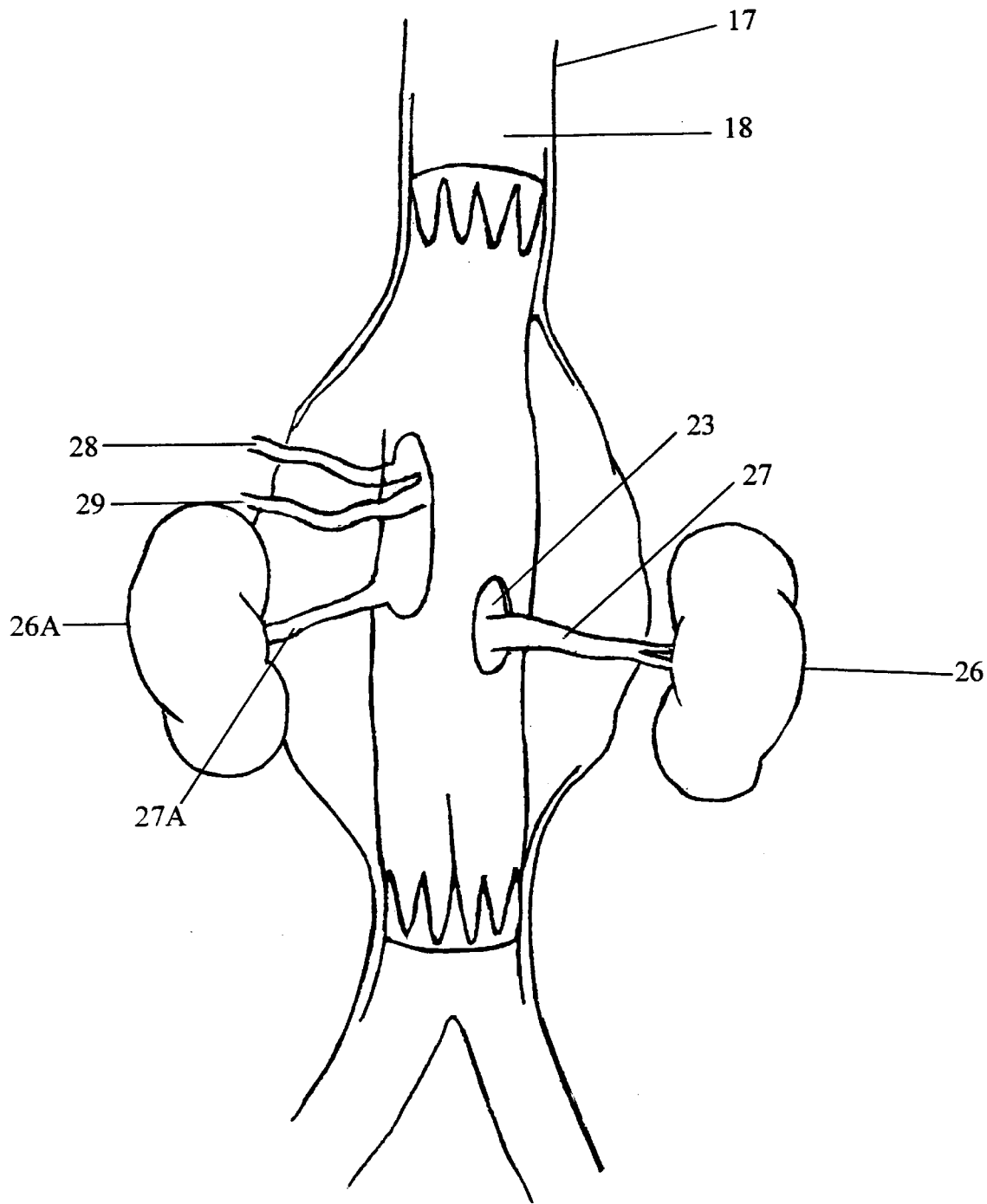
FIG. 5 is a partial sectional view of the graft and stent of the present invention interposed in the aorta at or around the intersection of the renal, stomach and bowel related arteries.

Similarly, adverting now to FIG. 5, the use of the present invention is shown with aorta 19 and kidneys 26 and 26A communicating with intersecting renal arteries 27 and 27A, as well as general bowel and stomach arteries 28 and 29. Stented graft 18 is shown to include, for example, lateral opening 23 positioned to accommodate renal artery 27 thereby ensuring blood flow to kidney 26 notwithstanding interposition of a stented graft in the aorta 19 at or around the intersecting point.

Figure 6:
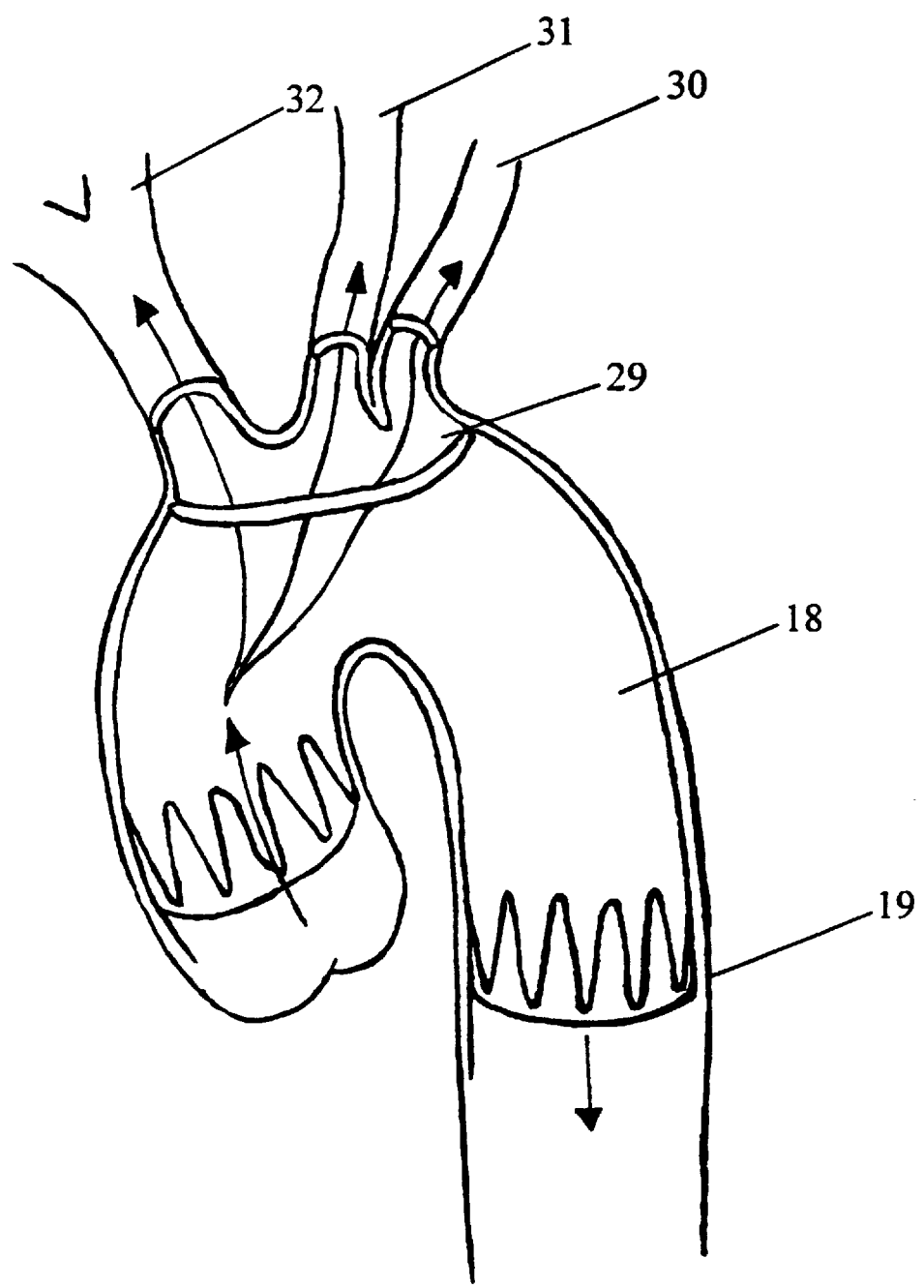
FIG. 6 is a view of the present stent and graft combination interposed within the descending aorta at or around the intersection of a series of cranial arteries leading to the brain.

Adverting next to FIG. 6, use of the present stented graft, 18, is shown within aorta 19 at or around the intersection of cranial arteries, 30, 31 and 32. Lateral opening 24 is shown to be positioned at a point of intersection among cranial arteries 30, 31 and 32 and aorta 19.

Figure 7:
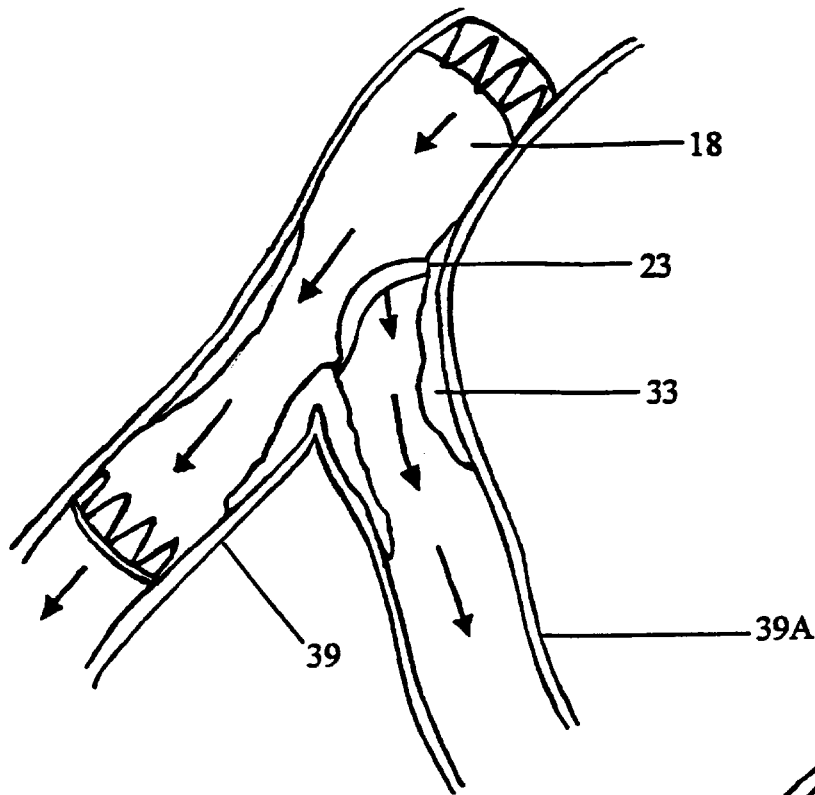
FIG. 7 is a view of the present invention interposed in the coronary artery.
Figure 8:
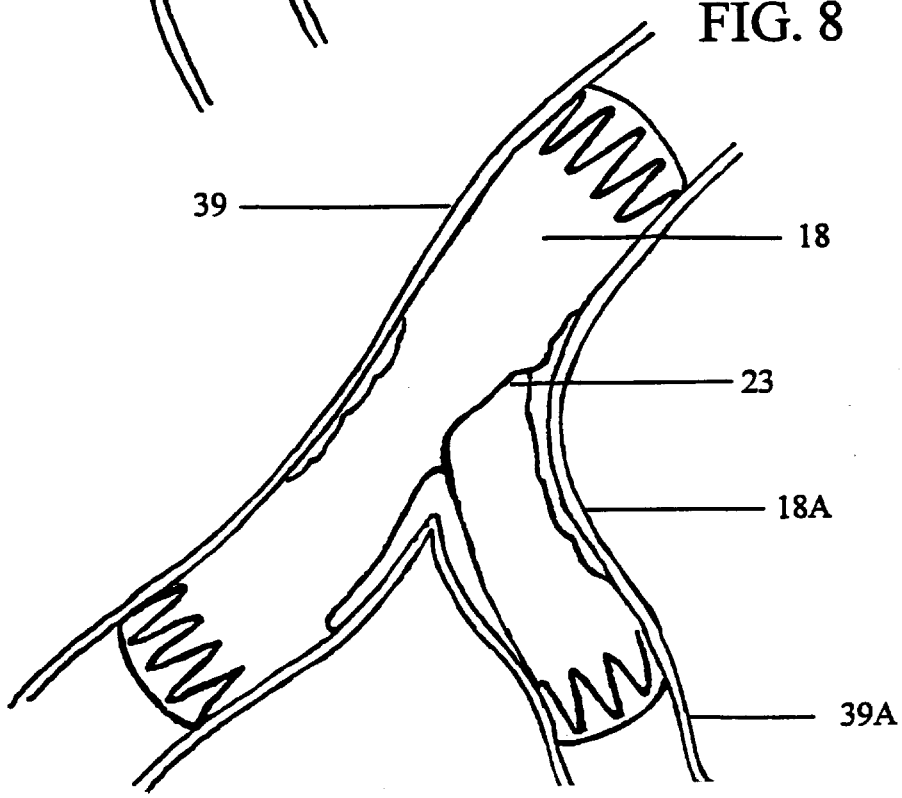
FIG. 8 is a view of the present invention interposed in the coronary artery and including a second stent.

Adverting next to FIGS. 7 and 8, use of the lateral opening technique is illustrated in connection with branches of the coronary artery, 39 and 39A. In particular, first graft 18 is inserted at the intersection point of coronary arteries 39 and 39A. Diseased portions 33 are shown to include both sections of artery 39 and 39A. Lateral opening 23 is positioned at the intersection point and the grafted stent 18 (or solely a graft) is appropriately positioned to ensure blood flow through both arteries 39 and 39A. Adverting to FIG. 8, a second stented graft (or solely a graft, 18A), is interposed through lateral opening 23 into artery 39A thereby completely treating diseased portion 33.

Accordingly, the present invention also contemplates the use of multiple stents, when required, to treat arterial disease encompassing both of two or more intersecting arteries. The present invention describes a stented graft and method that can be readily adapted and used for the surgical treatment of arterial disease at or around the point of intersection of two or more arteries and clearly solves many of the problems of the prior art by allows surgeons to employ the preferred grafted stent technique in an area where such technique was not before available or an option.

Many modifications to the invention would be apparent to one of skill in the art; for example, stent configurations and grafts of various dimensions, materials and size could easily be adapted for use with the invention. Moreover, positioning of the graft and stents, critical to the success of the invention, is shown to be accomplished with the use of a balloon catheter. Other methods of positioning the stent would equally be applicable without varying from the scope and purpose of the invention. These and other modifications to the invention fall well within the scope of the following claims and will be apparent to one of skill in the art.

What is claimed is:

1. A stent for the treatment of arterial disease at an intersection between a main artery and a lateral artery, the stent comprising:
   a) a main body portion adapted to be positioned in a main artery and comprising a surrounding side wall defining a passageway extending to a first opening and a second opening, wherein when the stent is positioned in the main artery, the passageway in the main body portion extending to the first opening and the second opening permits the flow of blood through the main artery;
   b) at least one lateral opening provided in the surrounding side wall of the main body portion and in fluid flow communication with the passageway extending to the first opening and the second opening; and
   c) a lateral support ring provided on the surrounding side wall of the main body portion to surround and define the one lateral opening, wherein the lateral support ring is sized to be larger than an opening of a lateral artery such that the lateral support ring is adapted to seat against a side wall of the main artery surrounding the intersection with the lateral artery when the stent is positioned in the main artery.

2. The stent of claim 1 wherein the stent is further adapted to be selectively contracted and expanded.

3. The stent of claim 1 wherein the stent is further adapted to receive a secondary stent within the at least one lateral opening.

4. The stent of claim 1 wherein the stent is adapted to fit within a graft and wherein the graft further comprises at least one lateral opening coincident with the one lateral opening of the stent and wherein blood is capable of flowing through the coincident lateral openings of the stent and the graft.

* * * * *